US012673011B2

(12) United States Patent
Yamada et al.

(10) Patent No.: US 12,673,011 B2
(45) Date of Patent: Jul. 7, 2026

(54) TWO-PHASE COMPOSITION

(71) Applicant: L'OREAL, Paris (FR)

(72) Inventors: Yukinori Yamada, Kawasaki (JP); Masanori Orita, Kawasaki (JP); Natsuno Mishina, Kawasaki (JP); Sho Watanabe, Kawasaki (JP)

(73) Assignee: L'OREAL, Paris (FR)

( * ) Notice: Subject to any disclaimer, the term of this patent is extended or adjusted under 35 U.S.C. 154(b) by 437 days.

(21) Appl. No.: 18/246,285

(22) PCT Filed: Sep. 10, 2021

(86) PCT No.: PCT/JP2021/034209
§ 371 (c)(1),
(2) Date: Mar. 22, 2023

(87) PCT Pub. No.: WO2022/065207
PCT Pub. Date: Mar. 31, 2022

(65) Prior Publication Data

US 2023/0355484 A1 Nov. 9, 2023

(30) Foreign Application Priority Data

Sep. 28, 2020 (JP) ................................ 2020-162247
Oct. 28, 2020 (FR) ...................................... 2011047

(51) Int. Cl.

| | |
|---|---|
| ***A61K 8/00*** | (2006.01) |
| ***A61K 8/03*** | (2006.01) |
| ***A61K 8/35*** | (2006.01) |
| ***A61K 8/39*** | (2006.01) |
| ***A61K 8/92*** | (2006.01) |
| ***A61Q 1/14*** | (2006.01) |

(52) U.S. Cl.
CPC .................. *A61K 8/03* (2013.01); *A61K 8/35* (2013.01); *A61K 8/39* (2013.01); *A61K 8/92* (2013.01); *A61Q 1/14* (2013.01); *A61K 2800/882* (2013.01)

(58) Field of Classification Search
None
See application file for complete search history.

(56) References Cited

U.S. PATENT DOCUMENTS

2001/0005508 A1 6/2001 Mui et al.
2014/0369943 A1* 12/2014 Pilz ..................... A61K 8/4946 424/59
2016/0143825 A1 5/2016 Pesaro et al.
2020/0163905 A1 5/2020 Mendrok-Edinger et al.

FOREIGN PATENT DOCUMENTS

| | | | |
|---|---|---|---|
| CN | 107072898 | A | 8/2017 |
| CN | 107198675 | A | 9/2017 |
| CN | 107997996 | A | 5/2018 |
| CN | 109276513 | A | 1/2019 |
| CN | 111358730 | A | 7/2020 |
| EP | 0370856 | A2 | 5/1990 |
| EP | 0603080 | A1 | 6/1994 |
| KR | 10-2020-0026939 | A | 3/2020 |
| RU | 2707282 | C2 | 11/2019 |

OTHER PUBLICATIONS

First Office Action mailed on Sep. 28, 2024, issued for the corresponding Chinese Patent Application No. 202180078362.0, 16 pages, with English translation.
Notice of Reasons for Refusal mailed on Oct. 15, 2024, issued for the corresponding Japanese Patent Application No. 2020-162247, 6 pages, with English translation.
International Search Report for the corresponding patent application No. PCT/JP2021/034209 dated Jan. 25, 2022.
Database GNPD [online], Mintel; Mar. 24, 2020, anonymous: Softener, XP055825354, Database accession No. 7437237.
Suncare Compositions ED, Darl Kuhn, ip.com, ip.com Inc., West Henrietta, NY, US, Jun. 23, 2019, XP013183608, pp. 42, 51.

* cited by examiner

*Primary Examiner* — Necholus Ogden, Jr.
(74) *Attorney, Agent, or Firm* — LUCAS & MERCANTI, LLP

(57) ABSTRACT

The present invention relates to a two-phase composition comprising an oil phase comprising (a) at least one oil, and an aqueous phase comprising: (b) at least one aromatic ketone compound represented by formula (I); (c) at least one polyglyceryl fatty acid ester; and (d) water. The composition according to the present invention has two visually distinct phases when not being mixed. However, the composition according to the present invention can be transformed into a single phase composition when being mixed. The single phase composition, such as an emulsion, can provide good cosmetic effects such as good make-up removability, without discomfort. The single phase composition can return to a two-phase composition with a clean interface between the two re-formed phases.

12 Claims, No Drawings

TWO-PHASE COMPOSITION

CROSS REFERENCE TO RELATED APPLICATION

This Application is a 371 of PCT/JP2021/034209 filed on Sep. 10, 2021 which, in turn, claimed the priority of Japanese Patent Application No. 2020-162247 filed on Sep. 28, 2020 and French Patent Application No. 2011047 filed on Oct. 28, 2020, all of which are incorporated herein by reference.

TECHNICAL FIELD

The present invention relates to a two-phase or bi-phase composition which has two visually distinct phases and is capable of transforming into a single phase composition that can transform again into the two-phase or bi-phase composition.

BACKGROUND ART

Compositions having two visually distinct phases, especially an aqueous phase and an oily phase, which are not emulsified in each other at rest, are generally referred to as "two-phase" (or "bi-phase") compositions. They differ from emulsions by the fact that, at rest, the two phases are separate and form a single interface between the two phases, instead of forming multiple interfaces between a continuous phase and each of the discontinuous phases which are present in emulsions.

Such two-phase compositions have already been described, for example, in EP-A-370 856 and EP-A-603 080, especially for removing make-up from around the eyes.

It is preferable that a two-phase composition before being used, i.e., at rest, be stable such that the aspect and/or smell of the composition can remain unchanged for a long period of time under various temperature and storage conditions.

When using, a two-phase composition requires mixing, such as shaking, in order to form a single phase composition, such as a "temporary" emulsion, which is then applied onto a keratin substance such as skin. This single phase composition needs to provide target cosmetic effects such as good make-up removability. It is preferable if the single phase composition can provide cosmetic effects without providing discomfort.

On the other hand, after being used, i.e., at rest, the single phase composition must regain its initial state by transforming into a two-phase composition, which is known as "phase separation". It is preferable that the interface between the re-formed two phases be clean such that no precipitation is present at the interface.

Thus, there is a need for a two-phase or bi-phase composition with two visually distinct phases which is stable when not being mixed, and can be transformed into a single phase composition when being mixed, wherein the single phase composition can provide good cosmetic effects such as good make-up removability, without discomfort, and can return to its initial state, i.e., a two-phase or bi-phase composition, with a clean interface between the two re-formed phases.

DISCLOSURE OF INVENTION

An objective of the present invention is to provide a two-phase composition which is stable, and can be transformed into a single phase composition when being mixed, wherein the single phase composition can provide good cosmetic effects such as good make-up removability, without discomfort, and can return to a two-phase composition with a clean interface between the two re-formed phases.

The above objective can be achieved by a two-phase composition comprising:

an oil phase comprising (a) at least one oil, and an aqueous phase comprising:

(b) at least one aromatic ketone compound represented by the following chemical formula (I)

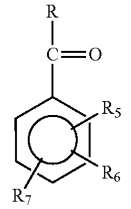

(I)

wherein $R_5$, $R_6$ and $R_7$, each independently, represent a hydrogen atom, a hydroxyl group, a $C_1$-$C_6$ alkyl group, or a $C_1$-$C_6$ alkoxy group, with the proviso that at least one of $R_5$, $R_6$ and $R_7$ represents a hydroxyl group, and R represents a $C_1$-$C_6$ alkyl group or an aryl group;

(c) at least one polyglyceryl fatty acid ester; and (d) water.

The composition according to the present invention can transform into a single phase composition. The single phase composition can transform into a two phase composition.

The (a) oil may be selected from non-polar oils, preferably selected from the group consisting of hydrocarbon oils, ether oils and mixtures thereof, and more preferably selected from the group consisting of volatile hydrocarbon oils, ether oils, and mixtures thereof.

The amount of the (a) oil(s) in the composition according to the present invention may be from 7% to 70% by weight, and preferably from 15% to 65% by weight, relative to the total weight of the composition.

The R in the chemical formula (I) may represent a methyl group, an ethyl group or a phenyl group, preferably a methyl group or a phenyl group, and more preferably a methyl group.

The (b) aromatic ketone compound may be hydroxyacetophenone, preferably monohydroxyacetophenone, and more preferably 4-hydroxyacetophenone.

The amount of the (b) aromatic ketone compound(s) in the composition according to the present invention may be from 0.1% to 3% by weight, preferably from 0.2% to 1% by weight, and more preferably from 0.3% to 0.5% by weight, relative to the total weight of the aqueous phase of the composition.

The (c) polyglyceryl fatty acid ester may be selected from polyglyceryl fatty acid diesters.

The (c) polyglyceryl fatty acid ester may comprise from 2 to 6 polyglyceryl units, preferably from 4 to 6 polyglyceryl units, and more preferably 5 or 6 polyglyceryl units.

The (c) polyglyceryl fatty acid ester may be selected from the group consisting of polyglyceryl-6 dicaprate, polyglyceryl-6 dioleate, polyglyceryl-6 distearate, and mixtures thereof.

The amount of the (c) polyglyceryl fatty acid ester(s) in the composition according to the present invention may be from 0.001% to 0.5% by weight, preferably from 0.005% to 0.1% by weight, and more preferably from 0.01% to 0.05% by weight, relative to the total weight of the aqueous phase of the composition.

The amount of the (d) water in the composition according to the present invention may be from 30% to 93% by weight, and preferably from 35% to 85% by weight, relative to the total weight of the composition.

The composition according to the present invention may be a cosmetic composition, preferably a cleansing cosmetic composition, and more preferably a cleansing cosmetic composition for skin and eyelashes.

The present invention also relates to a cosmetic process for a keratin substance, comprising:

mixing the composition according to the present invention to form a single phase composition; and applying the single phase composition onto the keratin substance.

BEST MODE FOR CARRYING OUT THE INVENTION

After diligent research, the inventors have discovered that it is possible to provide a two-phase composition which is stable, and can be transformed into a single phase composition by mixing when being used, wherein the single phase composition can provide good cosmetic effects such as good make-up removability, without discomfort, and can return to a two-phase composition with a clean interface between the two re-formed phases when not being used.

Thus, one of the aspects of the present invention relates to a two-phase composition comprising:

an oil phase comprising (a) at least one oil, and an aqueous phase comprising:

(b) at least one aromatic ketone compound represented by the following chemical formula (I)

(I)

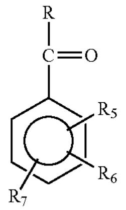

wherein $R_5$, $R_6$ and $R_7$, each independently, represent a hydrogen atom, a hydroxyl group, a $C_1$-$C_6$ alkyl group, or a $C_1$-$C_6$ alkoxy group, with the proviso that at least one of $R_5$, $R_6$ and $R_7$ represents a hydroxyl group, and R represents a $C_1$-$C_6$ alkyl group or an aryl group;

(c) at least one polyglyceryl fatty acid ester; and (d) water.

The composition according to the present invention has two visually distinct phases when not being mixed. However, the composition according to the present invention can be transformed into a single phase composition when being mixed. The single phase composition, such as an emulsion, can provide good cosmetic effects such as good make-up removability, without discomfort. The single phase composition can return to a two-phase composition with a clean interface between the two re-formed phases.

The composition according to the present invention is stable such that it can maintain an oil phase and an aqueous phase separately when not being mixed. Therefore, the two-phase or bi-phase aspect of the composition according to the present invention can be maintained during storage and the like of the composition according to the present invention.

In particular, the composition according to the present invention is stable such that the aspect and/or smell of the composition can remain unchanged for a long period of time under various temperature and storage conditions. For example, the composition according to the present invention is stable at a lower temperature, with or without shaking. Accordingly, the composition according to the present invention can be stored well, in particular at a lower temperature even during transportation by automobiles which may cause vibrations and the like.

When being used, the composition according to the present invention is mixed. The two phases in the composition according to the present invention are an oil phase comprising at least one oil and an aqueous phase comprising water. Therefore, when mixing the composition according to the present invention, one of the two phases can be dispersed in the other phase to form an O/W or a W/O composition, such as an O/W or a W/O emulsion, which is visually uniform or forms a single phase.

The mixing of the composition according to the present invention can be easily performed. For example, the mixing of the composition according to the present invention can be performed by shaking with the hands. After mixing the composition according to the present invention, the composition can form and maintain a single phase for a certain period of time without mixing again.

According to the present invention, the single phase composition formed by the two-phase composition can provide good cosmetic effects such as good make-up removability. Therefore, the composition according to the present invention can be used as a cosmetic composition, preferably a cleansing cosmetic composition, and more preferably a cleansing cosmetic composition for skin and eyelashes.

Further, the single phase composition formed by the two-phase composition according to the present invention can provide a good texture such as a smooth feeling to touch. In addition, it can provide less skin-scaling. The skin-scaling reflects the relatively large loss of the outer layer of the epidermis of skin, and can make the surface of the skin rough. Therefore, the composition according to the present invention can provide a smooth skin finish.

Furthermore, the single phase composition formed by the two-phase composition according to the present invention can be more comfortable, for example, it is less irritating. Therefore, the composition according to the present invention can be, for example, mild on the skin, in particular sensitive skin such as the skin around the eyes.

If the two-phase composition according to the present invention before being mixed is transparent, the single phase composition formed by mixing the two-phase composition can also be transparent.

The single phase composition formed by the two-phase composition according to the present invention can rapidly return to the two-phase composition again, after a certain period of time, by causing phase separation to re-form two visually distinct phases again. According to the present invention, the interface between the two re-formed phases can be clean such that no precipitation is present at the interface.

The composition according to the present invention is useful as, in particular, a make-up remover, preferably a make-up remover for keratin fibers, and more preferably a make-up remover for eyelashes, i.e., a mascara.

Hereafter, the composition according to the present invention will be described in a detailed manner.

[Composition]

(Oil)

The composition according to the present invention comprises (a) at least one oil. If two or more oils are used, they may be the same or different.

The (a) oil forms the oil phase of the composition according to the present invention.

Here, "oil" means a fatty compound or substance which is in the form of a liquid or a paste (non-solid) at room temperature (25° C.) under atmospheric pressure (760 mmHg). As the oils, those generally used in cosmetics can be used alone or in combination thereof. These oils may be volatile or non-volatile.

The oil may be a non-polar oil such as a hydrocarbon oil and a symmetric ether oil, a silicone oil, or the like; a polar oil such as a plant or animal oil as well as an ester oil and an asymmetric ether oil; or a mixture thereof.

The oil may be selected from the group consisting of oils of plant or animal origin, synthetic oils, silicone oils, hydrocarbon oils and fatty alcohols.

As examples of plant oils, mention may be made of, for example, meadowfoam oil, linseed oil, camellia oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils, and artificial triglycerides.

As an example of ether oils, mention may be made of dicaprylyl ether.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols, and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; and diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters, as well as pentaerythrityl tetraethyl hexanoate.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrityl tetra(2-ethylhexanoate), 2-ethylhexyl succinate, diethyl sebacate, and mixtures thereof.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate) (INCI name: Caprylic/Capric Triglyceride) and glyceryl tri(caprate/caprylate/linolenate).

As examples of silicone oils, mention may be made of, for example, linear organopolysiloxanes such as dimethylpolysiloxane (INCI name: Dimethicone), methyiphenylpolysiloxane, methylhydrogenpolysiloxane, and the like; cyclic organopolysiloxanes such as cyclohexasiloxane, octamethylcyclotetrasiloxane, decamethylcyclopentasiloxane, dodecamethylcyclohexasiloxane, and the like; and mixtures thereof.

Preferably, silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used according to the present invention are silicone oils as defined above and comprise in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof. Mention may also be made of cyclocopolymers of a type such as dimethylsiloxane/methylalkylsiloxane, such as Silicone Volatile® FZ 3109 sold by the company Union Carbide, of formula:

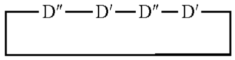

with

D'': 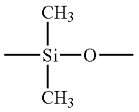 and with D': 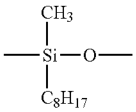

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane; and (ii) linear volatile polydialkylsiloxanes containing 2 to 9 silicon atoms and having a viscosity of less than or equal to $5\times10^{-6}$ $m^2/s$ at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 $mm^2/s$; and the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups, mention may be made of polydiarylsiloxanes, especially polydiphenylsiloxanes and polyalkylarylsiloxanes such as phenyl silicone oil.

The phenyl silicone oil may be chosen from the phenyl silicones of the following formula:

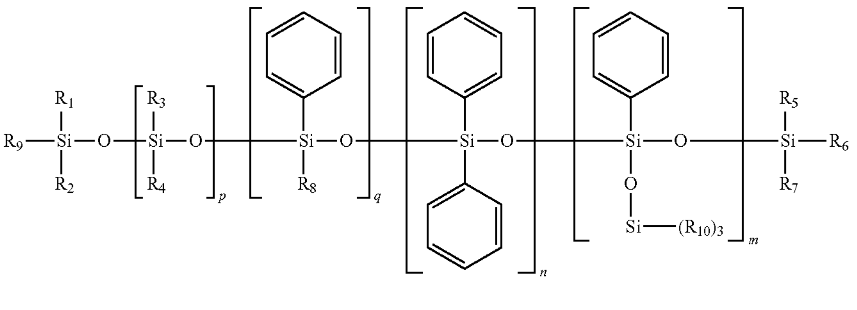

in which $R_1$ to $R_{10}$, independently of each other, are saturated or unsaturated, linear, cyclic or branched $C_1$-$C_{30}$ hydrocarbon-based radicals, preferably $C_1$-$C_{12}$ hydrocarbon-based radicals, and more preferably $C_1$-$C_6$ hydrocarbon-based radicals, in particular methyl, ethyl, propyl or butyl radicals, and m, n, p and q are, independently of each other, integers between 0 and 900 inclusive, preferably 0 and 500 inclusive, and more preferably 0 and 100 inclusive, with the proviso that the sum n+m+q is other than 0.

Examples that may be mentioned include the products sold under the following names:

- the Silbione® oils of the 70 641 series from Rhodia;
- the oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- certain oils of the SF series from General Electric, such as SF 1023, SF 1154, SF and SF 1265.

As the phenyl silicone oil, phenyl trimethicone ($R_1$ to $R_{10}$ are methyl; p, q, and n=0; m=1 in the above formula) is preferable.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:

- linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane; and
- linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosan, and decene/butene copolymer; and mixtures thereof.

The term “fatty” in the fatty alcohol means the inclusion of a relatively large number of carbon atoms. Thus, alcohols which have 4 or more, preferably 6 or more, and more preferably 12 or more carbon atoms are encompassed within the scope of fatty alcohols. The fatty alcohol may be saturated or unsaturated. The fatty alcohol may be linear or branched.

The fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may or may not be substituted with at least one hydroxyl group.

As examples of the fatty alcohol, mention may be made of lauryl alcohol, isostearyl alcohol, undecylenyl alcohol, octyldodecanol, hexyldecanol, oleyl alcohol, linoleyl alcohol, palmitoleyl alcohol, arachidonyl alcohol, and mixtures thereof.

Thus, the fatty alcohol may be selected from straight or branched, saturated or unsaturated $C_6$-$C_{30}$ alcohols, preferably straight or branched, saturated $C_6$-$C_{30}$ alcohols, and more preferably straight or branched, saturated $C_{12}$-$C_{20}$ alcohols.

The term “saturated fatty alcohol” here means an alcohol having a long aliphatic saturated carbon chain. It is preferable that the saturated fatty alcohol be selected from any linear or branched, saturated $C_6$-$C_{30}$ fatty alcohols. Among the linear or branched, saturated $C_6$-$C_{30}$ fatty alcohols, linear or branched, saturated $C_{12}$-$C_{20}$ fatty alcohols may preferably be used. Any linear or branched, saturated $C_{16}$-$C_{20}$ fatty alcohols may be more preferably used. Branched $C_{16}$-$C_{20}$ fatty alcohols may be even more preferably used.

As examples of saturated fatty alcohols, mention may be made of lauryl alcohol, isostearyl alcohol, undecylenyl alcohol, octyldodecanol, hexyldecanol, and mixtures thereof. In one embodiment, octyldodecanol and hexyldecanol can be used as a saturated fatty alcohol.

According to at least one embodiment, the fatty alcohol used in the composition according to the present invention is preferably chosen from octyldodecanol, hexyldecanol and mixtures thereof.

The (a) oil may be selected from non-polar oils, preferably selected from the group consisting of hydrocarbon oils, ether oils and mixtures thereof, and more preferably selected from the group consisting of volatile hydrocarbon oils, ether oils, and mixtures thereof.

The volatile hydrocarbon oil may be selected from volatile branched $C_8$-$C_{16}$ hydrocarbon oils, preferably selected from the group consisting of isohexadecane, isodecane, isododecane, and a mixture thereof.

It is preferable that ether oils be non-volatile. The ether oil may be selected from dialkyl ethers represented by the following formula $$R^1—O—R^2$$

wherein each of $R^1$ and $R^2$ independently denotes a linear, branched or cyclic $C_{4-24}$ alkyl group, preferably $C_{6-18}$ alkyl group, and more preferably $C_{8-12}$ alkyl group. It may be preferable that $R^1$ and $R^2$ are the same.

As the linear alkyl group, mention may be made of a butyl group, a pentyl group, a hexyl group, a heptyl group, an octyl group, a nonyl group, a decyl group, an undecyl group, a dodecyl group, tridecyl group, a tetradecyl group, a pentadecyl group, a hexadecyl group, a heptadecyl group, an octadecyl group, a nonadecyl group, an eicosyl group, a behenyl group, a docosyl group, a tricosyl group, and an tetracosyl group.

As the branched alkyl group, mention may be made of a 1-methylpropyl group, 2-methylpropyl group, a t-butyl group, a 1,1-dimethylpropyl group, a 3-methylhexyl group, a 5-methylhexyl group, an 1-ethylhexyl group, an 2-ethylhexylgroup, a 1-butylpentyl group, a 5-methyloctyl group, an 1-ethylhexyl group, an 2-ethylhexyl group, a 1-butylpentyl group, a 5-methyloctyl group, a 2-butyloctyl group, an isotridecyl group, a 2-pentylnonyl group, a 2-hexyldecyl group, an isostearyl group, a 2-heptylundecyl group, an 2-octyldodecyl group, a 1,3-dimethylbutyl group, a 1-(1-methylethyl)-2-methylpropyl group, a 1,1,3,3-tetramethylbutyl group, a 3,5,5-trimethylhexyl group, a 1-(2-methylpropyl)-3-methylbutyl group, a 3,7-dimethyloctyyl group, and a 2-(1,3,3-trimethylbutyl)-5,7,7-trimethyloctyl group.

As the cyclic alkyl group, mention may be made of a cyclohexyl group, a 3-methylcyclohexyl group, and a 3,3,5-trimethylcyclohexyl group.

It may be preferable that the ether oil be selected from the group consisting of dicaprylyl ether, dicapryl ether, dilauryl ether, diisostearyl ether, dioctyl ether, nonyl phenyl ether, dodecyl dimethylbutyl ether, cetyl dimethylbutyl ether, cetyl isobutyl ether, and mixtures thereof.

It may be more preferable that the ether oil be selected from the group consisting of dicaprylyl ether, dicapryl ether, dilauryl ether, diisostearyl ether, dioctyl ether, and mixtures thereof.

The amount of the (a) oil in the composition according to the present invention may be 7% by weight or more, and preferably 15% by weight or more, relative to the total weight of the composition.

The amount of the (a) oil in the composition according to the present invention may be 70% by weight or less, and preferably 65% by weight or less, relative to the total weight of the composition, with the proviso that the amount of the (a) oil is not zero.

The amount of the (a) oil in the composition according to the present invention may be from 7% to 70% by weight, and preferably from 15% to 65% by weight, relative to the total weight of the composition.

(Aromatic Ketone Compound)

The composition according to the present invention comprises (b) at least one aromatic ketone compound. If two or more (b) aromatic ketone compounds are used, they may be the same or different.

The (b) aromatic ketone compound is represented by the following chemical formula (I)

(I)

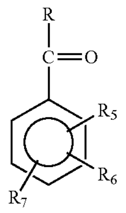

wherein $R_5$, $R_6$ and $R_7$, each independently, represent a hydrogen atom, a hydroxyl group, a $C_1$-$C_6$ alkyl group, or a $C_1$-$C_6$ alkoxy group, with the proviso that at least one of $R_5$, $R_6$ and $R_7$ represents a hydroxyl group, and R represents a $C_1$-$C_6$ alkyl group or an aryl group.

As the $C_1$-$C_6$ alkyl group, mention may be made of, for example, a methyl group, an ethyl group, and a propyl group. A methyl group is preferable.

As the $C_1$-$C_6$ alkoxy group, mention may be made of, for example, a methoxy group, an ethoxy group, and a propoxy group. A methoxy group is preferable.

As the aryl group, mention may be made of, for example, a phenyl group, a substituted phenyl group, a naphthyl group, and a substituted naphthyl group. As the substituent (s), mention may be made of a hydroxyl group and a $C_1$-$C_6$ alkyl group such as a methyl group. A phenyl group is preferable.

It is preferable that the R in the above chemical formula (I) represent a methyl group, an ethyl group or a phenyl group, preferably a methyl group or a phenyl group, and more preferably a methyl group.

As the (b) aromatic ketone compound, mention may be made of, for example, 2-hydroxyacetophenone,
3-hydroxyacetophenone,
4-hydroxyacetophenone,
2,5-dihydroxyacetophenone,
2,6-dihydroxyacetophenone,
4-hydroxy-3-methoxyacetophenone,
3,4,5-trihydroxyacetophenone,
2',2'-dihydroxybenzophenone,
2-hydroxybenzophenone,
2,2',4,4'-tetrahydroxybenzophenone, and
3,4,2',4',6'-pentahydroxybenzophenone.

It is preferable that the (b) aromatic ketone compound be hydroxyacetophenone, more preferably monohydroxyacetophenone, and even more preferably 4-hydroxyacetophenone.

The amount of the (b) aromatic ketone compound in the composition according to the present invention may be 0.1% by weight or more, preferably 0.2% by weight or more, and more preferably 0.3% by weight or more, relative to the total weight of the aqueous phase of the composition.

The amount of the (b) aromatic ketone compound in the composition according to the present invention may be 3% by weight or less, preferably 1% by weight or less and more preferably 0.5% by weight or less, relative to the total weight of the aqueous phase of the composition, with the proviso that the amount of the (b) aromatic ketone compound is not zero.

The amount of the (b) aromatic ketone compound in the composition according to the present invention may be from 0.1% to 3% by weight, preferably from 0.2% to 1% by weight, and more preferably from 0.3% to 0.5% by weight, relative to the total weight of the aqueous phase of the composition.

The amount of the (b) aromatic ketone compound in the composition according to the present invention may be 0.01% by weight or more, preferably 0.05% by weight or more, and more preferably 0.1% by weight or more, relative to the total weight of the composition.

The amount of the (b) aromatic ketone compound in the composition according to the present invention may be 5% by weight or less, preferably 3% by weight or less, and more preferably 1% by weight or less, relative to the total weight of the composition, with the proviso that the amount of the (b) aromatic ketone compound is not zero.

The amount of the (b) aromatic ketone compound in the composition according to the present invention may be from 0.01% to 5% by weight, preferably from 0.05% to 3% by weight, and more preferably from 0.1% to 1% by weight, relative to the total weight of the composition.

(Polyglyceryl Fatty Acid Ester)

The composition according to the present invention comprises (c) at least one polyglyceryl fatty acid ester. If two or more (c) polyglyceryl fatty acid esters are used, they may be the same or different.

The (c) polyglyceryl fatty acid ester may be chosen from the mono, di and tri esters of a linear or branched, saturated or unsaturated fatty acid, preferably saturated fatty acid, including from 2 to 28 carbon atoms, preferably from 4 to 20 carbon atoms, and more preferably from 6 to 12 carbon atoms, such as lauric acid, oleic acid, stearic acid, isostearic acid, capric acid, caprylic acid, and myristic acid.

It is preferable that the (c) polyglyceryl fatty acid ester have a polyglycerol moiety derived from 2 to 6 glycerols, more preferably from 4 to 6 glycerols, and even more preferably 5 or 6 glycerols. In other words, it is preferable that the (c) polyglyceryl fatty acid ester comprise from 2 to 6 polyglyceryl units, more preferably 4 to 6 polyglyceryl units, and even more preferably 5 or 6 polyglyceryl units.

In the composition according to the present invention, the (c) polyglyceryl fatty acid ester is present in the aqueous phase. Therefore, the (c) polyglyceryl fatty acid ester is relatively hydrophilic.

Thus, the (c) polyglyceryl fatty acid ester may have an HLB (Hydrophilic Lipophilic Balance) value of 8.0 or more, preferably 9.0 or more, and more preferably 10.0 or more. If two or more polyglyceryl fatty acid esters are used, the HLB value is determined by the weighted average of the HLB values of all the polyglyceryl fatty acid esters.

The term HLB ("hydrophilic-lipophilic balance") is well known to those skilled in the art, and reflects the ratio between the hydrophilic part and the lipophilic part in the molecule. HLB values can be calculated with the formula HLB=20*(1−S/A), where S is the saponification number of the ester and A is the neutralization number of the fatty acid.

The (c) polyglyceryl fatty acid ester may be selected from polyglyceryl fatty acid monoesters.

The polyglyceryl fatty acid monoester may have an HLB value of from 8.0 to 17.0, preferably from 9.0 to 16.0, and more preferably from 10.0 to 15.0. If two or more polyglyceryl fatty acid monoesters are used, the HLB value is determined by the weighted average of the HLB values of all the polyglyceryl fatty acid monoesters.

The polyglyceryl fatty acid monoester may be selected from the group consisting of PG4 oleate (HLB: 8.8), PG4 laurate (HLB: 10.3), PG4 isostearate (HLB: 8.2), PG5 laurate (HLB: 10.5), PG6 isostearate (HLB: 10.8), PG4 caprylate (HLB: 14), PG4 caprate (HLB: about 15), PG5 myristate (HLB: 15.4), PG5 stearate (HLB: 15), PG5 oleate (HLB: 12.2), PG6 caprylate (HLB: 14.6), PG6 caprate (HLB: 13.1), PG6 laurate (HLB: 14.1) and mixtures thereof.

It is preferable for the (c) polyglyceryl fatty acid ester be selected from polyglyceryl fatty acid diesters.

The polyglyceryl fatty acid diester may have an HLB value of from 8.0 to 13.0, preferably from 9.0 to 12.0, and more preferably from 10.0 to 11.0. If two or more polyglyceryl fatty acid diesters are used, the HLB value is determined by the weighted average of the HLB values of all the polyglyceryl fatty acid diesters.

The polyglyceryl fatty acid diester may be selected from the group consisting of PG-6 distearate (HLB: 8), PG-6 dioleate (HLB: 9.8), PG-6 dicaprate (HLB: 10.2), and mixtures thereof.

As PG6 dicaprate, for example, Sunsoft Q-102H-C marketed by Taiyo Kagaku Co., Ltd. may be used. As PG6 dioleate, Sunsoft Q-172H-C marketed by Taiyo Kagaku Co. Ltd. may be used. As PG6 distearate, Emalex DSG-6 marketed by Nihon Emulsion Co., Ltd. may be used.

The amount of the (c) polyglyceryl fatty acid ester in the composition according to the present invention may be 0.001% by weight or more, preferably 0.005% by weight or more, and more preferably 0.01% by weight or more, relative to the total weight of the aqueous phase of the composition.

The amount of the (c) polyglyceryl fatty acid ester in the composition according to the present invention may be 0.5% by weight or less, preferably 0.1% by weight or less and more preferably 0.05% by weight or less, relative to the total weight of the aqueous phase of the composition, with the proviso that the amount of the (c) polyglyceryl fatty acid ester is not zero.

The amount of the (c) polyglyceryl fatty acid ester in the composition according to the present invention may be from 0.001% to 0.5% by weight, preferably from 0.005% to 0.1% by weight, and more preferably from 0.01% to 0.05% by weight, relative to the total weight of the aqueous phase of the composition.

The amount of the (c) polyglyceryl fatty acid ester in the composition according to the present invention may be 0.0001% by weight or more, preferably 0.0005% by weight or more, and more preferably 0.001% by weight or more, relative to the total weight of the composition.

The amount of the (c) polyglyceryl fatty acid ester in the composition according to the present invention may be 1% by weight or less, preferably 0.5% by weight or less and more preferably 0.1% by weight or less, relative to the total weight of the composition, with the proviso that the amount of the (c) polyglyceryl fatty acid ester is not zero.

The amount of the (c) polyglyceryl fatty acid ester in the composition according to the present invention may be from 0.0001% to 1% by weight, preferably from 0.0005% to 0.5% by weight, and more preferably from 0.001% to 0.1% by weight, relative to the total weight of the composition.

(Water)

The composition according to the present invention comprises (d) water.

The (d) water can form an aqueous phase of the composition according to the present invention.

The amount of the (d) water in the composition according to the present invention may be 30% by weight or more, and preferably 35% by weight or more, relative to the total weight of the composition.

The amount of the (d) water in the composition according to the present invention may be 93% by weight or less, and preferably 85% by weight or less, relative to the total weight of the composition, with the proviso that the amount of the (d) water is not zero.

The amount of the (d) water in the composition according to the present invention may be from 30% to 93% by weight, and preferably from 35% to 85% by weight, relative to the total weight of the composition.

(Ester of Citric Acid)

The composition according to the present invention may comprise (e) at least one ester of citric acid. If two or more esters of citric acid are used, they may be the same or different.

The (e) ester of citric acid may be represented by the following chemical formula (I):

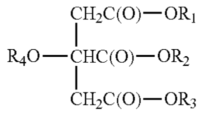

(I)

wherein $R_1$, $R_2$ and $R_3$ independently represent a hydrogen atom, a saturated or unsaturated, linear or branched $C_1$-$C_{30}$ hydrocarbon group, or a saturated or unsaturated cyclic $C_3$-$C_{30}$ hydrocarbon group, wherein at least one of $R_1$, $R_2$ and $R_3$ is not a hydrogen atom, and $R_4$ represents a hydrogen atom or an $R'_4$—CO— group in which $R'_4$ represents a saturated or unsaturated, linear or branched $C_1$-$C_8$ hydrocarbon group, or a saturated or unsaturated cyclic $C_3$-$C_8$ hydrocarbon group.

It is preferable that all of $R_1$, $R_2$ and $R_3$ be a saturated or unsaturated, linear or branched $C_1$-$C_{30}$ hydrocarbon group, or a saturated or unsaturated cyclic $C_3$-$C_{30}$ hydrocarbon group, more preferably a saturated or unsaturated, linear or branched $C_1$-$C_{30}$ hydrocarbon group, and even more preferably a linear or branched $C_1$-$C_{30}$ alkyl group.

It is preferable that $R_4$ be a hydrogen atom or an $R'_4$—CO— group in which $R'_4$ represents a saturated or unsaturated, linear or branched $C_1$-$C_8$ hydrocarbon group, more preferably a hydrogen atom or an $R'_4$—CO— group in which $R'_4$ represents a linear or branched $C_1$-$C_8$ alkyl group, and even more preferably a hydrogen atom or an $R'_4$—CO— group in which $R'_4$ represents a methyl group.

It may be preferable that the (e) ester of citric acid be selected from the group consisting of triethyl citrate, tributyl citrate, trioctyl citrate, triethyl acetylcitrate, tribuyl acetylcitrate, tri(2-ethylhexyl) acetylcitrate, and a mixture thereof, more preferably the group consisting of triethyl citrate, tributyl citrate, triethyl acetylcitrate, tribuyl acetylcitrate, and a mixture thereof, and even more preferably ethyl citrate.

The amount of the (e) ester(s) of citric acid in the composition according to the present invention may be 0.1% by weight or more, preferably 0.5% by weight or more, and more preferably 1% by weight or more, relative to the total weight of the composition.

The amount of the (e) ester(s) of citric acid in the composition according to the present invention may be 15% by weight or less, preferably 10% by weight or less and more preferably 5% by weight or less, relative to the total weight of the composition, with the proviso that the amount of the (b) ester(s) of citric acid is not zero.

The amount of the (e) ester(s) of citric acid in the composition according to the present invention may be from 0.1% to 15% by weight, preferably from 0.5% to 10% by weight, and more preferably from 1% to 5% by weight, relative to the total weight of the composition.

(Cosmetic Active Ingredient)

The composition according to the present invention may comprise at least one cosmetic active ingredient. A single type of the cosmetic active ingredient, or two or more different types of the cosmetic active ingredient may be used in combination.

The cosmetic active ingredient may preferably be water-insoluble or oil-insoluble.

The amount of the cosmetic active ingredient in the composition according to the present invention may be 0.1% by weight or more, preferably 0.5% by weight or more, and more preferably 1% by weight or more, relative to the total weight of the composition.

The amount of the cosmetic active ingredient in the composition according to the present invention may be 30% by weight or less, preferably 25% by weight or less, and more preferably 20% by weight or less, relative to the total weight of the composition, with the proviso that the amount of the cosmetic active ingredient is not zero.

The amount of the cosmetic active ingredient in the composition according to the present invention may range from 0.1% to 30% by weight, preferably from 0.5% to 25% by weight, and more preferably from 1% to 20% by weight, relative to the total weight of the composition.

(Surfactant)

The composition according to the present invention may comprise at least one additional surfactant which is different from the (c) polyglyceryl fatty acid ester. If two or more additional surfactants are used, they may be the same or different.

However, it may be preferable that the amount of the additional surfactant is small.

The amount of the additional surfactant may be 1% by weight or less, preferably 0.5% by weight or less, and more preferably 0.3% by weight or less, relative to the total weight of the composition according to the present invention. It is in particular preferable that the composition according to the present invention comprise no additional surfactant.

(Other Ingredients)

The composition according to the present invention may also include at least one optional or additional ingredient.

The amount of the optional or additional ingredient(s) is not limited, but may be from 0.01% to 30% by weight, preferably from 0.1% to 20% by weight, and more preferably from 1% to 10% by weight, relative to the total weight of the composition according to the present invention.

The optional or additional ingredient(s) may be selected from the group consisting of anionic, cationic, nonionic, or amphoteric polymers; organic or inorganic UV filters; peptides and derivatives thereof; protein hydrolyzates; swelling agents; penetrating agents; thickeners; suspending agents; sequestering agents; opacifying agents; dyes; vitamins or provitamins; fragrances; preservatives, co-preservatives, stabilizers; and mixtures thereof.

The composition according to the present invention may include one or several cosmetically acceptable organic solvents, which may be alcohols: in particular monovalent alcohols such as ethyl alcohol, isopropyl alcohol, benzyl alcohol, and phenylethyl alcohol; diols such as ethylene glycol, propylene glycol, and butylene glycol; other polyols such as glycerol, sugar, and sugar alcohols; and ethers such as ethylene glycol monomethyl, monoethyl, and monobutyl ethers, propylene glycol monomethyl, monoethyl, and monobutyl ethers, and butylene glycol monomethyl, monoethyl, and monobutyl ethers.

The organic solvent(s) may then be present in a concentration of from 0.01% to 20% by weight, preferably from 0.1% to 15% by weight, and more preferably from 1% to 10% by weight, relative to the total weight of the composition.

The pH of the composition according to the present invention may be controlled. The pH may be, for example, from 3 to 11, preferably from 3.5 to 9, and more preferably from 4 to 7.

The pH may be adjusted to the desired value using at least one acidifying agent and/or at least one basifying agent.

The acidifying agents can be, for example, mineral or organic acids, for instance hydrochloric acid, orthophosphoric acid, carboxylic acid, for instance tartaric acid, citric acid, lactic acid, or sulphonic acids.

The basifying agent can be, for example, ammonium hydroxide, alkali metal hydroxide, alkali earth metal hydroxide, alkali metal carbonates, alkanolamines such as mono-, di-, and triethanolamines, and also their derivatives, preferably sodium or potassium hydroxide and compounds of the formula below:

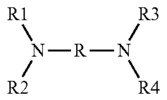

wherein

R denotes an alkylene such as propylene optionally substituted by a hydroxyl or a $C_1$-$C_4$ alkyl radical, and $R_1$, $R_2$, $R_3$, and $R_4$ independently denote a hydrogen atom, an alkyl radical, or a $C_1$-$C_4$ hydroxyalkyl radical, which may be exemplified by 1,3-propanediamine and derivatives thereof. Arginine, urea, and monoethanolamine may be preferable.

The acidifying or basifying agent may be present in an amount ranging from less than 5% by weight, preferably from 1% by weight or less, and more preferably from 0.1% by weight or less, relative to the total weight of the composition.

(Form)

The composition according to the present invention can have two visually distinct phases. One of the two phases is an oil phase, and the other is an aqueous phase.

The amount of the oil phase in the composition according to the present invention may be 20% by weight or more, preferably 30% by weight or more, and more preferably 40% by weight or more, relative to the total weight of the composition.

The amount of the oil phase in the composition according to the present invention may be 80% by weight or less, preferably 70% by weight or less and more preferably 60% by weight or less, relative to the total weight of the composition, with the proviso that the amount of the oil phase is not zero.

The amount of the oil phase in the composition according to the present invention may be from 20% to 80% by weight, preferably from 30% to 70% by weight, and more preferably from 40% to 60% by weight, relative to the total weight of the composition.

The oil phase comprises (a) at least one oil as explained above.

The amount of the (a) at least one oil in the oil phase may be 85% by weight or more, preferably 90% by weight or more, and more preferably 95% by weight of more, relative to the total weight of the oil phase.

The amount of the aqueous phase in the composition according to the present invention may be 20% by weight or more, preferably 30% by weight or more, and more preferably 40% by weight or more, relative to the total weight of the composition.

The amount of the aqueous phase in the composition according to the present invention may be 80% by weight or less, preferably 70% by weight or less and more preferably 60% by weight or less, relative to the total weight of the composition, with the proviso that the amount of the oil phase is not zero.

The amount of the aqueous phase in the composition according to the present invention may be from 20% to 80% by weight, preferably from 30% to 70% by weight, and more preferably from 40% to 60% by weight, relative to the total weight of the composition.

The aqueous phase comprises (b) at least one aromatic ketone compound, (c) at least one polyglyceryl fatty acid ester, and (d) water.

The amount of the (d) water in the aqueous phase may be 85% by weight or more, preferably 90% by weight or more, and more preferably 95% by weight of more, relative to the total weight of the aqueous phase.

In addition, the aqueous phase can comprise at least one additional hydrophilic ingredient. In one embodiment, the aqueous phase may comprise at least one pH adjuster such as an acid and a base, and/or at least one organic solvent such as diol.

The composition according to the present invention can be transformed into a single phase composition when being mixed. The composition according to the present invention after mixing can be of the O/W type or W/O type, preferably in the form of an O/W or W/O liquid composition, and more preferably in the form of an O/W or W/O emulsion.

If the specific gravity of the oil phase is smaller than that of the aqueous phase, the oil phase is present on the aqueous phase, in the composition according to the present invention. Typically, the oil phase is present on the aqueous phase, at rest, because the specific gravity of oil tends to be smaller than that of water.

[Preparation]

The composition according to the present invention can be prepared by forming an oil phase by providing (a) oil or mixing the ingredients, which include (a) oil(s), for the oil phase, forming an aqueous phase by mixing the ingredients, which include (b) aromatic ketone compound, (c) polyglyceryl fatty acid ester, and (d) water, for the aqueous phase, and combining the oil phase and the aqueous phase.

For example, the composition according to the present invention can be prepared by the process comprising:

(i) providing or mixing
  (a) at least one oil
  with at least one optional ingredient to form an oil phase;
(ii) mixing
  (b) at least one aromatic ketone compound;
  (c) at least one polyglyceryl fatty acid ester; and
  (d) water
  with at least one optional ingredient to form an aqueous phase; and
(iii) combining the oil phase and the aqueous phase.

The mixing step can be performed by any conventional means.

It is preferable that the step of combining the oil phase and the aqueous phase be performed gently such that the oil phase and the aqueous phase are slowly poured into a vessel such as a container.

[Use and Process]

When using the composition according to the present invention, it will be mixed by, for example, shaking with the hands (hand-shaking). After mixing the composition according to the present invention, the composition can form a single phase composition. The single phase composition can be applied onto a keratin substance to perform target cosmetic effects.

The keratin substance may be skin, nails, mucosae such as lips, or keratin fibers such as eyebrow and eyelashes.

The composition according to the present invention may preferably be used as a cosmetic composition, more preferably a cleansing cosmetic composition, and even more preferably a cleansing cosmetic composition for skin and eyelashes.

The composition according to the present invention can provide cosmetic effects such as make-up removal.

The composition according to the present invention can also provide a good texture such as a smooth feeling to touch, and therefore, it can provide a smooth skin finish.

The composition according to the present invention is comfortable because it is less irritating, and it is mild on the skin, in particular sensitive skin such as the skin around the eyes.

The skin here encompasses facial skin, neck skin, and the scalp. The composition according to the present invention may also be used for mucosae such as lips.

The composition according to the present invention can be used as it is (as a topical product), or can be used by being impregnated into a porous substrate such as a non-woven fabric preferably made from cellulose fibers such as cotton.

In particular, the composition according to the present invention may be intended for application onto a keratin substance such as skin, lips, eyebrows and eyelashes. Thus, the composition according to the present invention can be used for a cosmetic process for a keratin substance such as skin, lips, eyebrows and eyelashes, preferably skin and eyelashes.

The composition according to the present invention may be used for caring or cleansing, not for making up, a keratin substance. It is preferable that the composition according to the present invention be used for skin care products such as a lotion or cleansing products such as a make-up remover, not for make-up products such as a foundation. Preferably the composition according to the present invention does not comprise iron oxide, or comprises iron oxide in an amount of 0.5% by weight or less, more preferably 0.2% by weight or less, even more preferably 0.1% by weight or less, relative to the total weight of the composition according to the present invention.

The cosmetic process for a keratin substance according to the present invention may comprise, at least, the steps of mixing the composition according to the present invention to form a single phase composition; and applying the single phase composition onto the keratin substance.

The single phase composition does not have two visually distinct phases. Instead, the single phase composition has a single phase which is typically an emulsion phase. The emulsion phase may not be transparent, but it may be translucent or opaque.

The present invention may relate to the use of (b) at least one aromatic ketone compound, and (c) at least one polyglyceryl fatty acid ester;

in a two-phase composition comprising an aqueous phase comprising (d) water and an oil phase comprising (a) oil, in order to stabilize the composition, in particular at a lower temperature such as 4° C., and/or make the composition less irritative.

In addition, the present invention may also relate to the use of (b) at least one aromatic ketone compound, and (c) at least one polyglyceryl fatty acid ester;

in a two-phase composition comprising an aqueous phase comprising (d) water and an oil phase comprising (a) oil, in order to stabilize the composition, in particular at a lower temperature such as 4° C., such that no precipitation is present at the interface between the oil phase and the aqueous phase which are re-formed after mixing the two-phase composition, and/or make the composition less irritating, in particular less irritating on the skin around the eyes.

EXAMPLES

The present invention will be described in a more detailed manner by way of examples. However, these examples should not be construed as limiting the scope of the present invention. The examples below are presented as non-limiting illustrations in the field of the present invention.

Examples 1-7 and Comparative Examples 1-5

The following compositions according to Examples 1-7 and Comparative Examples 1-5 shown in Table 1 were prepared by mixing the ingredients shown in Table 1 as follows.

(1) mixing the ingredients of Oil Phase Preparation (OP Preparation in Table 1) at about 25° C. to form a uniform mixture of Oil Phase ingredients;

(2) mixing the ingredients of Aqueous Phase Preparation (AP Preparation in Table 1) at about 60° C. to form a uniform mixture of Aqueous Phase Preparation ingredients; and (3) pouring the above into a package in order of the Aqueous Phase Preparation ingredients, then the Oil Phase Preparation ingredients to mix them for each composition.

The actual mixing weight ratio of Oil Phase Preparation: Aqueous Phase Preparation was 50:50 for Examples 1-6 and Comparative Examples 1-5, and 15:85 for Example 7.

It should be noted that "hydroxyacetophenone" means 4-hydroxyacetophenone.

The numerical values for the amounts of the ingredients shown in Table 1 are all based on "% by weight" as active raw materials.

TABLE 1

| | | Ex. 1 | Ex. 2 | Ex. 3 | Ex. 4 | Ex. 5 | Ex. 6 | Ex. 7 | Comp. Ex. 1 | Comp. Ex. 2 | Comp. Ex. 3 | Comp. Ex. 4 | Comp. Ex. 5 |
|---|---|---|---|---|---|---|---|---|---|---|---|---|---|
| OP Preparation | Isohexadecane | 55 | 55 | 55 | 55 | 55 | 55 | 60 | 55 | 55 | 55 | 55 | 55 |
| | Dicaprylyl Ether | 20 | 20 | 20 | 20 | 20 | 20 | 40 | 20 | 20 | 20 | 20 | 20 |
| | Isododecane | 23 | 23 | 23 | 23 | 23 | 23 | — | 23 | 23 | 23 | 23 | 23 |
| | Triethyl Citrate | 2 | 2 | 2 | 2 | 2 | 2 | — | 2 | 2 | 2 | 2 | 2 |
| | Total | 100 | 100 | 100 | 100 | 100 | 100 | 100 | 100 | 100 | 100 | 100 | 100 |
| AP Preparation | Hydroxyacetophenone | 0.5 | 0.5 | 0.5 | 0.5 | 0.5 | 0.3 | 0.5 | 0.5 | — | — | 0.5 | 0.5 |
| | Polyaminopropyl Biguanide | — | — | — | — | — | — | — | — | 0.5 | — | — | — |
| | Benzyl Alcohol | — | — | — | — | — | — | — | — | — | 0.23 | — | — |
| | Benzalkonium Chloride | — | — | — | — | — | — | — | — | — | 0.05 | — | — |
| | Butylene Glycol | 2 | 2 | 2 | 2 | 2 | 2 | 2 | 2 | 2 | 2 | 2 | 2 |
| | Citric Acid | 0.04 | 0.04 | 0.04 | 0.04 | 0.04 | 0.04 | 0.04 | 0.04 | 0.04 | 0.04 | 0.04 | 0.04 |
| | Sodium Citrate | 0.11 | 0.11 | 0.11 | 0.11 | 0.11 | 0.11 | 0.11 | 0.11 | 0.11 | 0.1 | 0.11 | 0.11 |
| | Sodium Chloride | 0.5 | 0.5 | 0.5 | 0.5 | 0.5 | 0.5 | 0.5 | 0.5 | 0.5 | 0.5 | 0.5 | 0.5 |
| | Polyglyceryl-6 Dicaprate | 0.05 | 0.04 | 0.03 | 0.02 | 0.01 | 0.05 | 0.05 | — | 0.05 | 0.05 | — | — |
| | Decyl Glucoside | — | — | — | — | — | — | — | — | — | — | 0.21 | — |
| | Poloxamer 184 | — | — | — | — | — | — | — | — | — | — | — | 0.11 |
| | Myrtrimonium Bromide | 0.07 | 0.07 | 0.07 | 0.07 | 0.07 | 0.07 | 0.07 | 0.07 | 0.07 | 0.07 | 0.07 | 0.07 |
| | Triethyl Citrate | 2 | 2 | 2 | 2 | 2 | 2 | 2 | 2 | 2 | 2 | 2 | 2 |
| | Water | qsp 100 | qsp 100 | qsp 100 | qsp 100 | qsp 100 | qsp 100 | qsp 100 | qsp 100 | qsp 100 | qsp 100 | qsp 100 | qsp 100 |
| | Total | 100 | 100 | 100 | 100 | 100 | 100 | 100 | 100 | 100 | 100 | 100 | 100 |
| | Actual OP/AP Weight Ratio | 50/50 | 50/50 | 50/50 | 50/50 | 50/50 | 50/50 | 15/85 | 50/50 | 50/50 | 50/50 | 50/50 | 50/50 |

OP: Oil Phase

AP: Aqueous Phase

TABLE 2

| | Ex. 1 | Ex. 2 | Ex. 3 | Ex. 4 | Ex. 5 | Ex. 6 |
|---|---|---|---|---|---|---|
| Make-up Removability | Excellent | Excellent | Excellent | Excellent | Excellent | Excellent |
| Transparency | Excellent | Excellent | Excellent | Excellent | Excellent | Excellent |
| Transparency after Shaking | Excellent | Excellent | Excellent | Excellent | Excellent | Excellent |
| Precipitation on Interface | No | No | No | No | No | No |
| Skin-Scaling | 3.9 | 4.0 | 4.0 | 4.2 | 4.2 | 3.9 |
| Mildness on Eyes | 3.9 | 4.0 | 3.9 | 4.0 | 3.9 | 4.2 |
| Demulsification Speed | 10'20" | 15'10" | 17'20" | 18'10" | 19'20" | 17'40" |
| Storage Stability (4° C.) | Excellent | Excellent | Excellent | Excellent | Excellent | Excellent |
| Storage Stability (25° C.) | Excellent | Excellent | Excellent | Excellent | Excellent | Excellent |
| Storage Stability (45° C.) | Excellent | Excellent | Excellent | Excellent | Excellent | Excellent |
| Storage Stability (4° C. Shaken Everyday) | Excellent | Excellent | Excellent | Excellent | Excellent | Excellent |
| Smoothness | 3.6 | 3.7 | 4.0 | 4.0 | 4.2 | 4.0 |
| | Ex. 7 | Comp. Ex. 1 | Comp. Ex. 2 | Comp. Ex. 3 | Comp. Ex. 4 | Comp. Ex. 5 |
| Make-up Removability | Excellent | Excellent | Excellent | Excellent | Excellent | Excellent |
| Transparency | Excellent | Excellent | Excellent | Excellent | Excellent | Excellent |
| Transparency after Shaking | Excellent | Poor | Excellent | Excellent | Poor | Poor |
| Precipitation on Interface | No | Yes | No | No | Yes | Yes |
| Skin-Scaling | 4.4 | 4.1 | 3.7 | 3.8 | 3.2 | 3.1 |
| Mildness on Eyes | 3.9 | 4.1 | 2.1 | 1.9 | 2.8 | 3.1 |
| Demulsification Speed | 5'10" | 21'50" | 14'20" | 15'40" | 26'40" | 24'50" |
| Storage Stability (4° C.) | Excellent | Poor | Excellent | Excellent | Poor | Poor |
| Storage Stability (25° C.) | Excellent | Good | Excellent | Excellent | Good | Good |
| Storage Stability (45° C.) | Excellent | Excellent | Excellent | Excellent | Excellent | Excellent |
| Storage Stability (4° C. Shaken Everyday) | Excellent | Poor | Good | Good | Good | Poor |
| Smoothness | 4.2 | 4.3 | 3.7 | 3.8 | 4.0 | 4.1 |

[Evaluation]

The compositions according to Examples 1-7 and Comparative Examples 1-5 were evaluated as follows.

(Make-Up Removability)

Each of 5 panelists made-up their eyelashes by applying a mascara product (MAYBELLINE Volum'Express Hypercurl Waterproof N 01 Black) to the eyelashes with a brush with a total of 40 strokes (each time, the brush was dipped into a bottle including the mascara product).

4 mL of each of the compositions according to Examples 1-7 and Comparative Examples 1-5 was shaken to form an emulsion. By using a cotton sheet, the emulsion was applied onto the skin around the eyes by massaging with a circular movement of the cotton sheet around the eyes for 30 seconds.

The panelists evaluated the make-up removability with a grade of from 1 (very poor) to 5 (excellent), and the average of the evaluations was categorized in accordance with the following criteria.

Excellent (5.0 to 4.0): A mascara residue was not observed at all.

Good (3.9 to 3.0): A mascara residue was mostly not observed.

Poor (2.9 to 2.0): A mascara residue was slightly observed.

Very Poor (1.9 to 1.0): A mascara residue was observed.

The results are shown in Table 2.

(Transparency)

The transparency of each of the compositions according to Examples 1-7 and Comparative Examples 1-5, just after being prepared (before being shaken), was checked.

The results are shown in Table 2.

(Transparency after Shaking)

The transparency of each of the compositions according to Examples 1-7 and Comparative Examples 1-5, one week after shaking at 4° C., was checked.

The results are shown in Table 2.

(Precipitation on Interface)

The presence of precipitation on the interface between the oil phase and the aqueous phase of each of the compositions according to Examples 1-7 and Comparative Examples 1-5, one week after shaking at 4° C., was checked.

The results are shown in Table 2.

(Skin Scaling)

4 mL of each of the compositions according to Examples 1-7 and Comparative Examples 1-5 was shaken to form an emulsion. Using a cotton sheet, the emulsion was applied onto the skin around the eyes by massaging with a circular movement of the cotton sheet around the eyes for 30 seconds.

The panelists evaluated how much skin-scaling there was with a grade of from 1 (skin-scaling is more visible) to 5 (skin-scaling is less visible), and the scores of the grades were averaged.

The results are shown in Table 2.

(Mildness to Eyes)

4 mL of each of the compositions according to Examples 1-7 and Comparative Examples 1-5 was shaken to form an emulsion. Using a cotton sheet, the emulsion was applied onto the skin around the eyes by massaging with a circular movement of the cotton sheet around the eyes for 30 seconds.

The panelists evaluated discomfort during the above application with a grade of from 1 (very discomfort) to 5 (no discomfort), and the scores of the grades were averaged.

The results are shown in Table 2.

(Demulsification Speed)

Each of the compositions according to Examples 1-7 and Comparative Examples 1-5 was filled into a transparent glass bottle. The transparent bottle was shaken very well to form an emulsion. The transparent bottle was left to stand (at rest), and the time for the emulsion to disappear completely to form two visually distinct phases was measured.

The results are shown in Table 2.

(Stability)

Each of the compositions according to Examples 1-7 and Comparative Examples 1-5 was filled into a transparent glass bottle. The transparent bottle was held under temperature conditions of 4° C., 25° C., and 45° C. for 2 months. At 4° C., the bottle was kept at rest or shaken every day.

After 2 months, each composition was checked in terms of transparency, color, and odor, and evaluated in accordance with the following criteria.

Excellent: Almost the same conditions as production.

Good: Small changes in transparency, color, and odor were observed.

Poor: Changes in transparency, color, and odor were clearly observed. Either precipitation or a turbid aspect was also clearly observed.

Very Poor: Changes in transparency, color, and odor were remarkably observed. Either precipitation or a turbid aspect was also remarkably observed.

The results are shown in Table 2.

(Smoothness)

4 mL of each of the compositions according to Examples 1-7 and Comparative Examples 1-5 was shaken to form an emulsion. Using a cotton sheet, the emulsion was applied onto the skin around the eyes by massaging with a circular movement of the cotton sheet around the eyes for 30 seconds.

The panelists evaluated the smoothness on the skin after the above application with a grade of from 1 (very unsmooth=sticky) to 5 (very smooth), and the scores of the grades were averaged.

The results are shown in Table 2.

SUMMARY

Examples 1-7 show that the use of a combination of hydroxyacetophenone (4-hydroxyacetophenone) and polyglyceryl-6 dicaprate in an aqueous phase of a two-phase composition including an oil phase and the aqueous phase contributed to good stability, in particular good stability at a lower temperature, of the two-phase composition; and mildness to the skin around the eyes, high make-up removal efficacy, and smooth skin finish (as well as less skin-scaling) of the single phase composition formed by the two phase composition, and that the single phase composition was able to rapidly return to a two phase composition with a clean interface between the two re-formed phases.

Comparative Example 1 shows that no use of polyglyceryl-6 dicaprate deteriorated the stability at a lower temperature such as 4° C., and that small precipitations appeared at the interface between the two re-formed phases.

Comparative Examples 2 and 3 show that no use of hydroxyacetophenone caused strong discomfort around the eyes.

Comparative Examples 4 and 5 show that the use of other types of surfactants instead of polyglyceryl-6 dicaprate, deteriorated the stability at a lower temperature such as 4° C., and that small precipitations appeared at the interface between the two re-formed phases. Also, Comparative Examples 4 and 5 caused discomfort around the eyes.

The invention claimed is:

1. A two phase composition comprising:

an oil phase comprising (a) at least one oil selected from the group consisting of volatile branched C8-C16 hydrocarbon oils, dialkyl ether oils having two C8-12 alkyl groups, and mixtures thereof;

an aqueous phase comprising:

(b) at least one aromatic ketone compound represented by the following chemical formula (I)

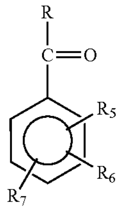

(I)

wherein $R_5$, $R_6$ and Ry, each independently, represent a hydrogen atom, a hydroxyl group, a $C_1$-$C_6$ alkyl group, or a $C_1$-$C_6$ alkoxy group, with the proviso that at least one of $R_5$, $R_6$ and $R_7$ represents a hydroxyl group, and R represents a $C_1$-$C_6$ alkyl group or an aryl group;

(c) at least one polyglyceryl fatty acid ester is selected from the group consisting of polyglyceryl-6 dicaprate, polyglyceryl-6 dioleate, polyglyceryl-6 distearate, and mixtures thereof; and (d) water.

2. The composition according to claim 1, wherein the composition is capable of transforming into a single phase composition.

3. The composition according to claim 2, wherein the single phase composition is capable of transforming into a two phase composition.

4. The composition according to claim 1, wherein the amount of the (a) oil(s) in the composition is from 7% to 70% by weight, relative to the total weight of the composition.

5. The composition according to claim 1, wherein the R in the chemical formula (I) represents a methyl group, an ethyl group or a phenyl group.

6. The composition according to claim 1, wherein the (b) aromatic ketone compound is hydroxyacetophenone.

7. The composition according to claim 1, wherein the amount of the (b) aromatic ketone compound(s) in the composition is from 0.1% to 3% by weight, relative to the total weight of the aqueous phase of the composition.

8. The composition according to claim 1, wherein the amount of the (c) polyglyceryl fatty acid ester(s) in the composition is from 0.001% to 0.5% by weight, relative to the total weight of the aqueous phase of the composition.

9. The composition according to claim 1, wherein the amount of the (d) water in the composition is from 30% to 93% by weight, relative to the total weight of the composition.

10. The composition according to claim 1, wherein the composition is a cosmetic composition.

11. A cosmetic process for a keratin substance, comprising:

mixing the composition according to claim 1 to form a single phase composition; and applying the single phase composition onto the keratin substance.

12. The composition according to claim 1, wherein the (a) oil is selected from the group consisting of isohexadecane, isododecane, dicaprylyl ether, and a mixture thereof.

* * * * *